US00PP12736P2

(12) United States Plant Patent
Lamb

(10) Patent No.: US PP12,736 P2
(45) Date of Patent: Jul. 2, 2002

(54) CALATHEA PLANT NAMED 'DOTTIE'

(75) Inventor: Anne E. Lamb, Sebring, FL (US)

(73) Assignee: Twyford Plant Laboratories, Inc., Sebring, FL (US)

( * ) Notice: Subject to any disclaimer, the term of this patent is extended or adjusted under 35 U.S.C. 154(b) by 56 days.

(21) Appl. No.: 09/656,223

(22) Filed: Sep. 6, 2000

(51) Int. Cl.[7] ..... A01H 5/00
(52) U.S. Cl. ..... Plt./375
(58) Field of Search ..... Plt./375, 373

*Primary Examiner*—Bruce R. Campell
*Assistant Examiner*—June Hwu
(74) *Attorney, Agent, or Firm*—Foley & Lardner

(57) ABSTRACT

A Calathea plant named 'Dottie' having nearly black green round leaves marked with vivid pink. The pink markings on the leaves do not fade as the plant matures.

2 Drawing Sheets

BACKGROUND OF THE INVENTION

The present invention comprises a new and distinct variety of Calathea, botanically known as *Calathea roseo picta,* and hereinafter referred to by the cultivar name, 'Dottie'.

The new variety is a naturally occurring mutation of the species *Calathea roseo picta* discovered and selected by the inventor Ann E. Lamb from tissue culture derived *C. roseo picta* in Apopka, Fla., Mar. 11 of 1998. Propagation by tissue culture and division done by the inventor was used to increase the number of plants for evaluation and has demonstrated the stability of the combination of characteristics as herein described generation to generation.

BRIEF DESCRIPTION OF THE DRAWINGS

The accompanying color photographic illustrations show typical characteristics of an 8-month-old plant of 'Dottie' (Sheet 1) grown in a 15.5 cm pot initiated from one microcutting obtained by tissue culture and grown under appropriate growing conditions, with colors being as nearly true as possible with illustrations of this type.

Sheet 2 shows an unnamed plant of the parent species *Calathea roseo picta* (unpatented) from which the new variety 'Dottie' is derived.

DETAILED DESCRIPTION OF THE NEW VARIETY

The following traits have been repeatedly observed and are determined to be basic characteristics of 'Dottie' which in combination distinguish this Calathea as a new and distinct cultivar:

1. The leaf surfaces of 'Dottie' are very dark black-green with bright pink markings.
2. The markings on the leaves of 'Dottie' remain vivid pink as the plant matures.
3. 'Dottie' has not been observed under all possible environmental conditions. The phenotype may vary significantly with variations in the environment such as temperature, light intensity, and daylength, without however, any change in the genotype.

Of the commercial varieties known to the present inventor, the most similar in comparison to 'Dottie' is its parent species *Calathea roseo picta.* 'Dottie' is similar to its parent species in growth habit, growth rate and pattern. However, unlike the species, its leaf surfaces very dark black-green with vivid pink markings. The markings on the leaves of 'Dottie' remain vivid pink as the plant matures, unlike those of the parent species which fade to silver-green with maturity.

The following observations, measurements and values describe plants grown in Apopka, Fla. under greenhouse conditions which closely approximate those generally used in horticultural practice. All color references are measured against The Royal Horticultural Society Colour Chart. Colors are approximate as color depends on horticultural practices such as light level and fertilization rate, among others, without, however any variance in genotype.

Classification: *Calathea roseo picta,* cv. 'Dottie'.

Origin: Mutation discovered among tissue culture derived *Calathea roseo picta.*

Propagation: Vegetative by tissue culture or division.

Plant: Under appropriate growing conditions, plant attains a size of approximately 10 cm to 13 cm in height and approximately 34 cm to 36 cm in width.

Leaves:

*Form.*—The leaf blade is orbicular with a mucronate tip and an obtuse base. The margins are entire. The midrib tends to be straight, or curved upward slightly over the length of the leaf. The leaf blade is wavy over the width of the leaf.

*Texture.*—Upper leaf surface smooth, shiny; lower leaf surface smooth, dull sheen.

*Size.*—Leaf blades are approximately 12.2 cm to 14.8 cm in length and approximately 11.5 cm to 14.5 cm in width.

*Petiole.*—The petiole is approximately 5.9 cm to 7.0 cm in length from the base of the petiole to the base of the leaf blade on the primary shoot. Secondary shoots are somewhat smaller depending on the age of the shoot. The petiole is approximately 4 mm in diameter just below the geniculum. The portion of the petiole below the geniculum is straight.

*Petiole sheath.*—The petiole sheath is approximately 5.5 cm in length and approximately 7 mm in width at their midpoint. The tip of the petiole sheath is rounded. There is approximately 5 mm to 1 cm between the top of the sheath and the base of the geniculum.

*Geniculum.*—The geniculum is approximately 1 cm in length, approximately 4 mm in diameter. The color is greener than but closest to 177 A. The orientation of the leaf to the petiole is variable, as the geniculum bends. During the night and early morning, the geniculum is straight, and the leaf is held upright above the petiole. During the day, the geniculum is bent, and the leaf is oriented approximately 90 degrees to the petiole.

*Veins.*—Veins and midrib are sunken, with the leaf blade slightly concave between veins on the upper surface. The midrib protrudes from the lower surface. Primary veins on leaves radiate out from the midrib along the length of the leaf. Veins are recessed within the leaf. There are approximately 12–14 primary veins on the leaf.

Color/pattern: The upper leaf surface is nearly black green in the center, and along the margins. It is marked with a band of bright pink which encircles the leaf approximately 1 cm to 2 cm from the margin. The leaf midrib and the tissues immediately surrounding the midrib are bright pink. The coloration of newly emerged leaves is somewhat lighter than for fully expanded leaves.

*Newly emerged leaves upper surface.*—Leaf center and margin lighter but closest to black, RHS 202 A, tinged with 147 A. Pink markings and midrib RHS 59 D.

*Newly emerged leaves lower surface.*—Leaf blade RHS 187 A, midrib RHS 187 A; petiole RHS 187 A; sheath varies between RHS 187 A and RHS 187 B.

*Fully expanded leaves upper surface.*—Leaf Center and margin black RHS 202 A, tinged with 147 A. Pink markings and midrib varies between RHS 59 C and RHS 59 D.

*Fully expanded leaves lower surface.*—Leaf Blade — darker than, but closest to RHS 187 A. Midrib — darker and greener than, but closest to RHS 187 A.

*Petiole.*—Dark anthocyanous RHS 187 A.

*Petiole sheath.*—Lighter than, but closest to RHS 187 A.

Inflorescence: The inflorescence of 'Dottie' is typical of the species *Calathea roseo picta* and is without commercials significance.

*Type.*—Short, terminally bracted spike.

*Length.*—Approximately 10 cm in length, measured from the basal attachment point to the tallest point of the inflorescence.

*General shape/arrangement.*—Bracts are arranged in closely spaced vertical ranks, and occupy the uppermost 5 cm of the spike. The uppermost bracts are ovate in shape with acute tips. The lowermost bracts with underlying flowers/buds are obovate with an obtuse, to somewhat emarginated tip. The inflorescences are hidden under the leaves, and are typically not of commercial significance.

*Duration of inflorescence.*—Approximately 3 months, individual flowers last one day, total duration of flowering is about 8 weeks.

Flowers:

*Borne.*—Short branch spikes under bracts; each branch spike contains approximately 4 buds.

*Individual flowers.*—Approximately 40 flower buds per inflorescence. Calyx and corolla mostly concealed under bract; staminodes, style and anther prominently displayed.

*Calyx.*—3 sepals present, approximately 1.5 cm long, 2.5 mm wide; color RHS 145 D (both surfaces).

*Corolla.*—3 parted, approximately 3 cm long, 4 mm wide, color RHS 145 D (both surfaces).

*Staminodes.*—3 present, 2 staminodes approximately 3.5 cm long, 4 mm wide; 1 staminode 3.2 cm long, 4.5 mm wide, color 155D with RHS 78 C.

*Time of blooming.*—Flower spikes appear early in summer.

Reproductive organs:

*Ovary.*—Inferior, 3-celled, 3 mm long, color RHS 158 B.

*Style.*—3 cm long, color RHS 155 D.

*Stamen.*—1 present; filament 2 cm long; anther 2.5 mm long, color RHS 155 D.

Seed characteristics: Not observed.

Disease/pest resistance/susceptibility: No special observations made.

Roots: Dark brown fibrous roots with fine laterals.

I claim:

1. A new and distinct cultivar of Calathea plant named 'Dottie', as illustrated and described.

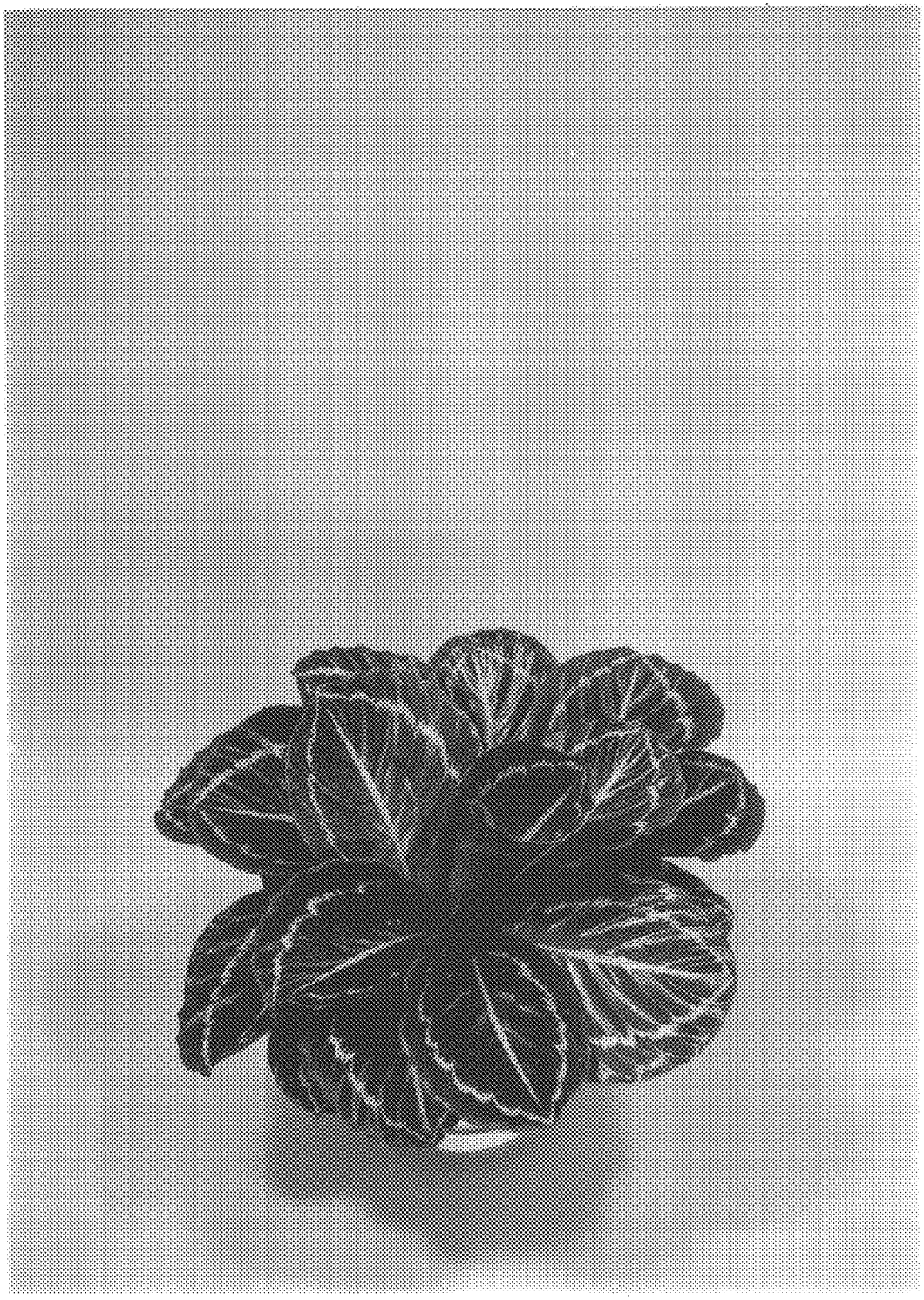

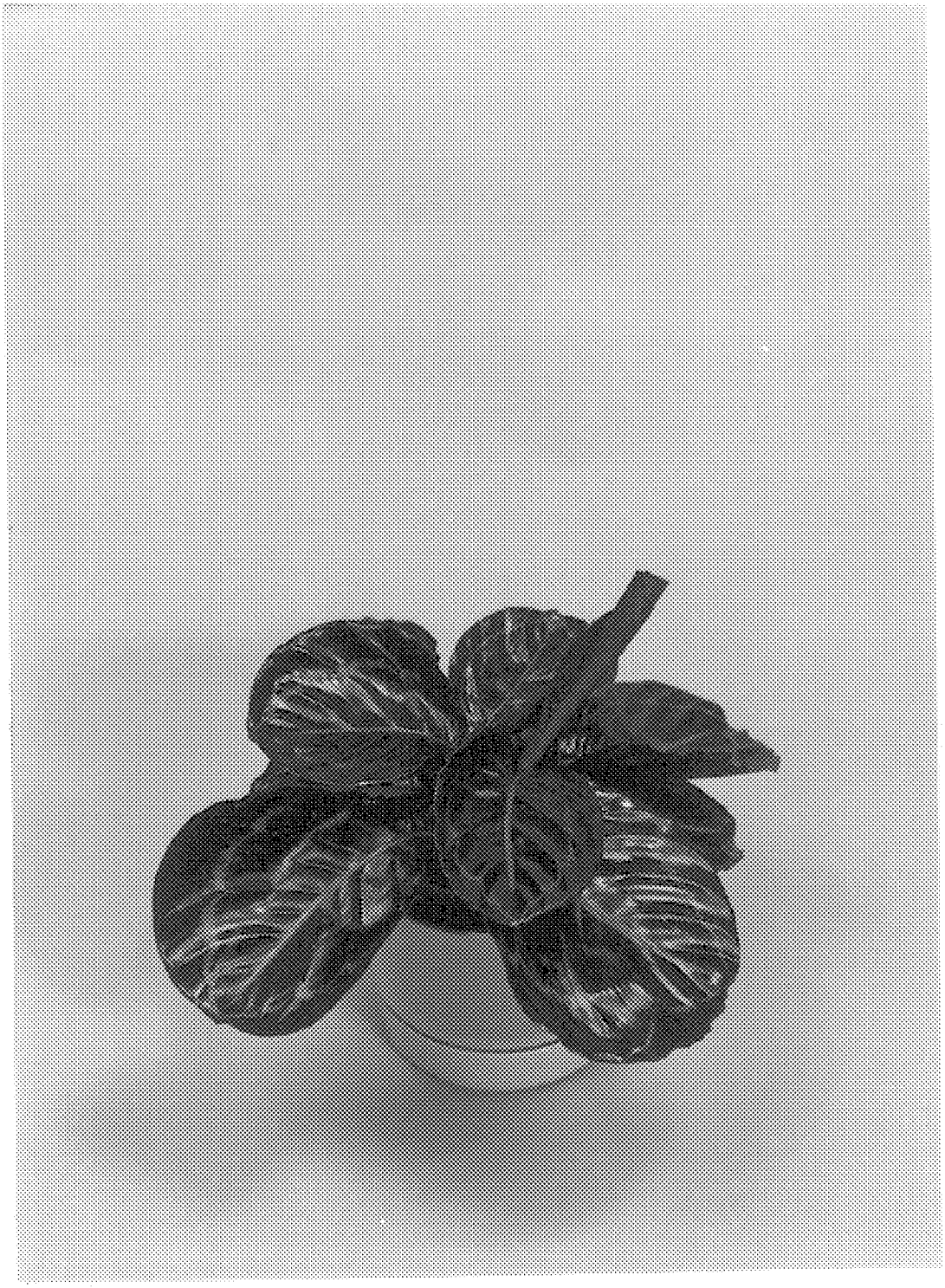

* * * * *